(12) United States Patent
Mandecki et al.

(10) Patent No.: US 8,785,352 B2
(45) Date of Patent: Jul. 22, 2014

(54) METAL NANOPARTICLE STRUCTURES FOR ENHANCING FLUORESCENCE-BASED ASSAYS

(75) Inventors: Wlodek Mandecki, Princeton, NJ (US); Ji Li, Hightstown, NJ (US); Zhuying Wang, Monmouth Junction, NJ (US)

(73) Assignee: Pharmaseq, Inc., Monmouth Junction, NJ (US)

( * ) Notice: Subject to any disclaimer, the term of this patent is extended or adjusted under 35 U.S.C. 154(b) by 0 days.

(21) Appl. No.: 13/643,875

(22) PCT Filed: Apr. 29, 2011

(86) PCT No.: PCT/US2011/034522
§ 371 (c)(1),
(2), (4) Date: Dec. 4, 2012

(87) PCT Pub. No.: WO2011/137325
PCT Pub. Date: Nov. 3, 2011

(65) Prior Publication Data
US 2013/0123118 A1      May 16, 2013

Related U.S. Application Data

(60) Provisional application No. 61/329,824, filed on Apr. 30, 2010.

(51) Int. Cl.
C40B 20/04 (2006.01)
G01N 21/64 (2006.01)
C40B 40/06 (2006.01)
C40B 40/10 (2006.01)

(52) U.S. Cl.
USPC .............. 506/4; 427/157; 427/402; 427/404; 506/16; 506/18

(58) Field of Classification Search
None
See application file for complete search history.

(56) References Cited

U.S. PATENT DOCUMENTS

| 7,211,440 B2 | 5/2007 | Blomberg et al. |
| 2009/0117006 A1 | 5/2009 | Fernandez |

FOREIGN PATENT DOCUMENTS

| DE | 10329195 A1 * | 1/2005 |
| WO | 2006052548 A1 | 5/2006 |
| WO | 2006138698 A2 | 12/2006 |
| WO | WO 2007007052 A2 * | 1/2007 |
| WO | 2009134527 A2 | 11/2009 |

OTHER PUBLICATIONS

Aslan et al., "Metal-enhanced fluorescence from silver nanoparticle-deposited polycarbonate substrates," J. Mater. Chem. 2006, 16:2846-2852.*
Kim et al., "Hard Coatings on Polycarbonate Plate by Sol-Gel Reaction of (3-glycidoxypropyl)trimethoxysilane," J. Korean Ind. Eng. Chem. 2006, 17:170-176.*

(Continued)

*Primary Examiner* — Samuel Woolwine
*Assistant Examiner* — Kaijiang Zhang
(74) *Attorney, Agent, or Firm* — Moser Taboada

(57) ABSTRACT

Provided, among other things, is a multiplex assay comprising: conducting a fluorescence-developing assay on microtabs having at least one surface that shows plasmonic enhancement, wherein a plurality of the microtabs have unique probes affixed to their plasmonically enhanced surfaces; and measuring the fluorescence associated with the substrates and identifying the correlated probe by for the microtab. The microtabs can be, for example, MTPs that send a unique identifier, and the correlated probe can be identified by querying the MTPs for their identifier.

17 Claims, 1 Drawing Sheet

(56) References Cited

OTHER PUBLICATIONS

Malicka et al., "Fluorescence spectral properties of cyanine dye-labeled DNA oligomers on surfaces coated with silver particles," Anal. Biochem. 2003, 317:136-146.*

Chiu et al., "Synergistic effects of epoxy- and amine-silanes on microarray DNA immobilization and hybridization," Biochem. J. 2003, 374:625-632.*

International Search Report and Written Opinion mailed Jan. 10, 2012 for PCT Application PCT/US2011/034522.

* cited by examiner

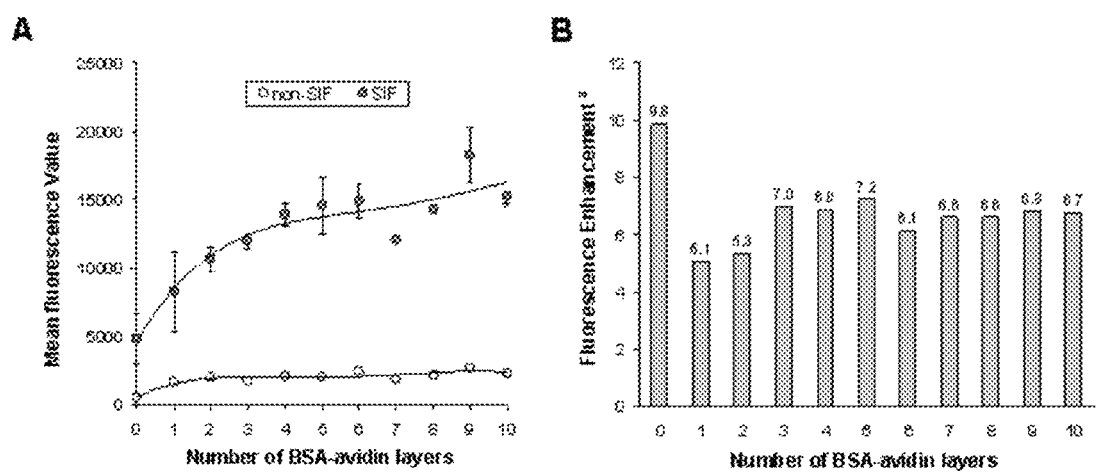

METAL NANOPARTICLE STRUCTURES FOR ENHANCING FLUORESCENCE-BASED ASSAYS

Embodiments of the present invention generally relate to methods and materials for enhancing the sensitivity of fluorescence-based assays with metal nanoparticles, such as silver or gold nanoparticles.

The use of metal nanoparticles to enhance fluorescence has been known for a number of years. It is believed that the effect is very distance-dependent, with fluorophore-metal distances below 40 Angstroms resulting in quenching, and with the enhancement gradually decreasing as distances go above 100 Angstroms. There are believed to be two mechanisms responsible for metal-enhanced fluorescence ("MEF", also known as "plasmonic enhancement"): the first is a locally enhanced field that increases the rate of excitation. The second is an interaction of excited fluorophore with nanoparticles. The effect of this interaction is a rapid release of the excitation energy and its radiation into free space. This emitter-antenna-like effect results in an increase in the quantum yield of the molecule and a decrease in its lifetime.

Given the tuning needed to achieve MEF, it has been hard to achieve particularly useful and reproducible enhancements in many contexts. Provided herein are methods of forming surfaces that are believed to aid in the more uniform distribution of metal particles on a surface, to provide a tool for helping achieve more reliable MEF results. Also provided are methods for placing metal particles on appropriate surfaces, and for further securing the metal particles on such surfaces. Such methods, applied with metal-modified small entities such as microchips, are unexpectedly resilient in the face of abrasive processing of the small entities, and thus make multiplex assay methods utilizing plasmonic enhancement. Further provided are compositions and methods for coating a surface.

SUMMARY

Provided, among other things, is a multiplex assay comprising: conducting a fluorescence-developing assay on microtabs having at least one surface that shows plasmonic enhancement, wherein a plurality of the microtabs have unique probes affixed to their plasmonically enhanced surfaces; and measuring the fluorescence associated with the substrates and identifying the correlated probe by for the microtab. The microtabs can be, for example, MTPs (defined below) that send a unique identifier, and the correlated probe can be identified by querying the MTPs for their identifiers.

Also provided is a fluorescence enhancing substrate comprising: a substrate; a first coating of AS/ES (defined below) on the substrate, wherein the coating is thicker than monolayer; and metal particles deposited or formed on the AS/ES coating, said particles effective to enhance a surface-mediated fluorescence assay by 5-fold or more.

Further provided is a fluorescence enhancing substrate comprising: a polymeric assay bead having surface pores; and metal particles deposited or formed on the surface of the bead, said particles effective to enhance a surface-mediated fluorescence assay by 5-fold or more.

Still further provided is an assay comprising: conducting a fluorescence-developing assay in a plurality of wells of a microtiter plate or with a nucleic acid/protein array, the microtiter wells or different regions of the array comprising substrates, wherein a plurality of the substrates have unique probes affixed thereto; and measuring the fluorescence associated with the substrates and identifying the correlated probe by location.

Also provided is a multiplex assay comprising: conducting a fluorescence-developing assay on microtabs having substrates, wherein a plurality of the microtabs have unique probes affixed to their substrates; and measuring the fluorescence associated with the substrates and identifying the correlated probe. The microtabs can be, for example, MTPs that send a unique identifier, and the correlated probe can be identified by querying the MTPs for their identifiers. Further provided is a polymer coating on a substrate comprising: the substrate; and the polymer coating formed from reacting AS and ES with the substrate, wherein AS is according to formula I (defined below); and ES is according to formula II (defined below).

Also provided is a method of forming polymer coating on a substrate comprising: reacting AS and ES with the substrate, wherein AS is according to formula I and ES is according to formula II.

Further provided is a method of forming a fluorescence enhancing substrate comprising: applying a first coating of AS/ES on the substrate, wherein the coating is thicker than monolayer; and depositing metal particles on the AS/ES coating by reducing metal salts, wherein said reduction-formed particles are effective to enhance a surface-mediated fluorescence assay by 5-fold or more.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

FIGS. 1(A and B) shows the relative distance independence of the fluorescence of certain embodiments of the invention. (A) The mean fluorescence intensity was obtained using Image J software from images taken from a fluorescence microscope equipped with a digital camera, and plotted against the number of BSA-avidin layers. Background fluorescence (MTPs incubated with unlabeled BSA) from non-SIF or SIF-MTPs has been subtracted. Standard deviation was calculated based on 3-4 MTPs, except the group marked by asterisk (SIF-MTP of layer #10) in which only 1 MTP was included. (B) Fluorescence enhancement as a function of the number of BSA-avidin layers. Fluorescence enhancement is the ratio of fluorescence intensity of SIF-MTPs to that of non-SIF-MTPs.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

Light-Triggered Transponders and Microtabs

As described in U.S. Pat. No. 7,098,394, very small, light-triggered transponders ("MTPs" or "p-Chips") are available to provide identifiers, for example as identifiers used in conjunction in nucleic acid assays (e.g., assays using DNA, RNA, or analogs thereof). These have proven to be stable under physiological conditions. Such devices have also provided a substrate on which new approaches for using metal particles have now been explored. (These transponders are a subset of "microtransponders.")

These MTPs are generally sided, in that the photocell/RF circuitry is formed on one face, and the other major face is generally silicon—and can be a product of height reduction by back grinding. The circuitry face is generally protected by a passivation layer, such as of silicon dioxide, silicon nitride or mixtures, or multiple such layers.

A MTP has a length, width and height. A planar MTP is one where the height is 50% or less than the smallest of the length or width. In some embodiments, the height is 40% or less, 35% or less, 30% or less, 25% or less, or 20% or less, than the smallest of the length or width. MTPs used in the invention are often, but not necessarily, square or rectangular, consistent with a focus on low cost of production. A MTP is one where the longest of the length or width is 1.2 mm or less. In some embodiment, the longest of the length or width is 1.1 mm or less, 1.0 mm or less, 0.9 mm or less, 0.8 mm or less, 0.7 mm or less, or 0.6 mm or less. or 0.5 mm or less, or 0.4 mm or less, or 0.3 mm or less. In one embodiment, the microchip is 600 micron×600 micron×100 or 120 micron.

A "microtab" is a small entity having at least one surface of a material that is a functional substrate for attaching probes and providing plasmonic enhancement, such as a surface of an AS/ES coating (such as described below). Microtabs used in the invention are often, but not necessarily, square or rectangular, consistent with a focus on low cost of production. A round bead of appropriate dimensions (e.g., microscopic) can be a microtab. A microtab is one where the longest of the length, width, height or diameter is 1.2 mm or less. In some embodiment, the longest of the length, width, height or diameter is 1.1 mm or less, 1.0 mm or less, 0.9 mm or less, 0.8 mm or less, 0.7 mm or less, or 0.6 mm or less. or 0.5 mm or less, or 0.4 mm or less, or 0.3 mm or less.

Polymer Sub-Coating

In one aspect, silane-based polymer is used to stabilize metal particles on a substrate.

The polymer coating of one aspect of the present invention is formed by reacting an amino spacer tri-ether silane compound ("AS") and an epoxy spacer tri-ether silane compound ("ES") with the surface to be coated, generally in the presence of a trace of water. While not being bound to theory, it is believed that the epoxy provides a crosslinking function that contributes to stability and/or thickness of the coating.

The nomenclature "sub-coating" is used for convenience; it does not imply that in all embodiments there is a top coating.

The AS can have a structure, for example, of:

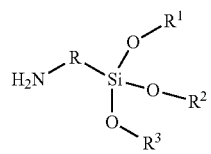

(I)

wherein R is a moiety of carbon, hydrogen and oxygen such that the linkage to the nitrogen is C—N, and the linkage to the silicon is C—Si; and wherein $R^1$, $R^2$ and $R^3$ are independently moieties of carbon, hydrogen and oxygen such that the linkage to the illustrated oxygen is C—O and the so-defined silicon ethers are reactive with silicate glass.

In certain embodiments, R is C1 to C12 alkyl or alkenyl, or C1 to C8, or C2 to C12, or C2 to C8. In certain embodiments, R is alkyl. In certain embodiments, $R^1$, $R^2$ and $R^3$ are independently C1 to C12 alkyl or alkenyl, or C1 to C8, or C1 to C6, or C1 to C4, or C1 to C3, or C2 to C12, or C2 to C8, or C2 to C6, or C2 to C4, or C2 to C3. In certain embodiments, $R^1$, $R^2$ and $R^3$ are alkyl. The AS can, for example, be aminopropyltrimethoxysilane or aminopropyltriethoxysilane.

The ES can have a structure, for example, of:

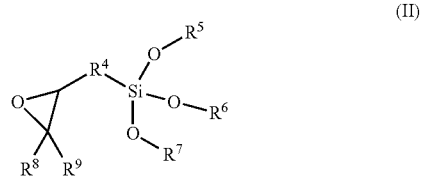

(II)

wherein $R^4$ is a moiety of carbon, hydrogen and oxygen such that the linkage to the silicon is C—Si; wherein $R^5$, $R^6$ and $R^7$ are independently moieties of carbon, hydrogen and oxygen such that the linkage to the illustrated oxygen is C—O and the so-defined silicon ethers are reactive with silicate glass; and wherein $R^8$ and $R^9$ are independently H or C1 to C4 alkyl.

In certain embodiments, $R^4$ is C1 to C12 alkyl or alkenyl, or C1 to C8, or C2 to C12, or C2 to C8. In certain embodiments, $R^4$ is alkyl. In certain embodiments, $R^5$, $R^6$ and $R^7$ are independently C1 to C12 alkyl or alkenyl, or C1 to C8, or C1 to C6, or C1 to C4, or C1 to C3, or C2 to C12, or C2 to C8, or C2 to C6, or C2 to C4, or C2 to C3. In certain embodiments, $R^5$, $R^6$ and $R^7$ are alkyl. In certain embodiments, no more than one of $R^8$ and $R^9$ is alkyl. The ES can, for example, be 3-glycidoxypropyltrimethoxysilane.

When the MTPs are coated, for example, the process can be conducted in an Eppendorf polypropylene tube. The MTPs can be washed, for example, with 0.5% (v/v) $H_2O$ in MeOH, which wash can be repeated multiple times. The MTPs can then be washed, for example, with 0.5-2% AS, 0.05-0.01% $H_2O$ in a dry solvent (e.g., toluene), which wash can be repeated multiple times. The primary reaction can then be conducted with 0.5-2% AS/ES, 0.05-0.01% $H_2O$ in a dry solvent, which reaction can be conducted at an elevated temperature, such as 60° C.-100° C. As will be recognized, these conditions can be adjusted based on, for example, the various boiling and decomposition temperatures, and the reactivities of the silane reagents. In certain embodiments, the reaction times are 1 hour-4 hour, where the reactant mixture can be exchanged with fresh reaction mixture one or more times during the reaction period. Ratios of AS:ES can be, in certain embodiments, 2:1-5:1 (molar).

Coatings produced with the above protocol can achieve similar densities in functional groups on the silicon and passivated sides of MTPs. The coatings can be more stable, such as stable enough at pH 4.5 to support aqueous coupling reactions. The coatings produce amino and hydroxy functionality, both of which can be utilized in further coupling reactions. The amino groups can be converted to carboxylic acid groups by reaction with acid anhydrides or equivalents (e.g., mono-N-hydroxysuccinamide esters of dicarboxylic acids), to create additional coupling functionalities.

Polymer coatings according to the invention are described by the reactants used to create them. However, claims to such coatings are not intended to be limited to the process of making the coatings. It is believed that at substantial expense greater compositional information could be obtained, but that such information is implied by the reactants, substrate, and reaction conditions. Accordingly, the claiming format is that which is practical, and one that implies composition.

In certain embodiments, coating layer is 0.1 micron or more, 0.2 micron or more, or 0.3 micron or more, or 0.4 micron or more, or 0.5 micron or more thick. In certain embodiments, the forming reaction is maintained or repeated until such thickness is achieved.

In one aspect, the unexpected relative independence of fluorescence from the number of BSA-avidin layers applied prior to a surface-mediated fluorescence assay is believed to be a surrogate for the complex surface structure of the polymer coatings. Regardless of theory, in one aspect, the invention is defined by such independence. When 1 to 10 layers are applied, the independence is seen if the ratio of (a) highest measured fluorescence enhancement (for one of the 1 to 10 layers) is to (b) the lowest measured fluorescence enhancement (for one of the 1 to 10 layers) is 2 or less, or 1.9 or less, or 1.8 or less, or 1.7 or less, or 1.6 or less, or 1.5 or less. In FIG. 1B, the highest is 7.2, and the lowest is 5.1, such that the ratio is about 1.4.

In certain embodiments, this layer-independence test is conducted on substrates that have received a polymer sub-coating and metal particles, but no polymer top coating. If the final product is to have a top coating, the effect can nonetheless be modeled on a comparable version without the top coating.

Polymer Deposition Substrates

Substrates for depositing the polymer coating include, for example, silicon and passivated microelectronic structures. Glass, silica or quartz can also be coated. Howarter and Youngblood, *Macromolecules*, 40 (2007) 1128-1132, indicate that additional substrates can be coated with aminopropyltriethoxysilane, such as polar polymers such as polyesters, polyamides, polycarbonates, polyimides, cellulosics, polyacrylics, and the like. Accordingly, the AS/ES coating process is believed to also provide an effective coating on substrates made of such polymers. For more hydrophobic polymers, such as polystyrene, numerous adsorbent coatings that provide more polar surfaces are known, and can be used as an intermediary to secure the AS/ES coating. Where, for example, a coating provides amine functionality, the amine can be converted to carboxylic acid, activated with N-hydroxysuccinamide, and reacted with an initial monolayer of AS. This initial coverage can anchor further coupling with AS/ES.

Applying Metal Particles to the Substrates

One method of applying metal particles is by forming a metal island film, such as using the methods described in Matveeva et al., *Anal. Chem.*, 334 (2004) 303-311 (for a silver island film). Metal island film can be formed by in situ reduction of metal salts, such as reduction with glucose.

Another method is by application of pre-formed particles with the substrate. The metal particles can be, for example, applied by an evaporation-mediated method. Or, the particles can be incubated with the substrate during a process of applying a second layer of polymer. It is believed that the texture of the polymer coating can limit the tendency of the particles to aggregate on surfaces. The particles can be pre-sized, such as with average diameters of 30 nm or more, 40 nm or more, 50 nm or more, 60 nm or more, 70 nm or more, 80 nm or more, 90 nm or more, or 100 nm or more. Or, they can be pre-sized, such as with average diameters of 120 nm or less, 100 nm or less, 90 nm or less, 80 nm or less, 70 nm or less, or 60 nm or less. Or, they can be pre-sized, such as with average diameters in a range implied by the above parameters.

Another method of particle application is to electrochemically deposit metal structures (e.g., silver). These structures often have fractal-like structure. In certain embodiments, these particles are applied to substrates that have not been coated with polymer, or which have been coated with thin coatings of AS or AS/ES polymer (such as coatings that are termed in the art "monolayer" coatings). These electrochemically deposited materials can be coated with a layer (or a further layer) of AS/ES polymer. The electrochemical deposition can use two electrodes applied against the substrate provide the electrons for electrochemical reduction. See, Shtoyko et al., *Anal. Chem.*, 80 (2008) 1962-1966; Goldys et al., *J. Am. Chem. Soc.*, 129 (2007) 12117-12122; Parfenov et al., *J. Phys. Chem. B*, 107 (2003) 8829-8833.

Application of the particles can be done in a dust-free, ultraclean environment, as this can limit contaminants which may nucleate larger aggregations of particles. Such larger aggregations can create inhomogeneities in particle distribution that may reduce fluorescence signal strength and/or reproducibility.

The metal used can, for example, be silver or gold. These are convenient formed by reduction or purchased as appropriately sized particles.

In certain embodiments, such as with MTPs or microtabs, only one surface is coated with polymer or metal. This sided coating can be accomplished by precoating (e.g., spin-coating) one surface of a wafer with a substance that does not allow the condensation of reagents, dicing the wafer to expose a surface, and then going through the regular coating procedure. Or, metal coating can be accomplished before a parent wafer is cut into MTPS or microtabs. In certain embodiments with MTPs or other microchips or micricrotabs (such as similarly sized microchips), the metal coating is localized to a face of the microchip other than that having the circuitry, such as the opposite major face of the microchip.

Polymer Top Coating

In certain embodiments, the AS/ES polymer is applied to the substrate (coated or uncoated with a base layer) after the application of metal particles. This coating can serve, for example, to stabilize or protect the metal particles. In certain embodiments, the top coating is applied under reaction conditions adapted to provide a thinner coating than is achieved with the subcoating. For example, where two 45 minute reactions with AS/ES are used to provide the subcoating, a 20 min. reaction under the same conditions might be used to provide the top coating.

In certain embodiments, any appropriate coating polymer is applied after the application of metal particles. For example, alky acrylates (e.g., methyl methacrylate or methyl acrylate) or other polymerization-ready monomers are applied to form a coating polymer by spin coating or by fluidized bed, or pre-formed polymers dissolved in a volatile carrier solvent are applied by such methods.

Distance Independence of Fluorescence Enhancement

It is well known that the distance between silver particles and the fluorophore is important for fluorescence enhancement. As outlined in the Examples, the fluorescence enhancement of a metal-particle composition on the AS/ES polymer is not substantially dependent on the number of BSA-biotin-avidin layers from 1 layer to 10 layers, a range that provides a classic measure of this dependence. In certain embodiments, the fluorescence enhancement of the silver particle coated materials of the invention is substantially independent of BSA-biotin-avidin layers. A recital of substantial independence from BSA-biotin-avidin layers means in the 1 to 10 layer range.

Reagent Attachment

The AS/ES coating provides amine and hydroxy functionality. All or a portion of the amine can be converted to carboxy by reaction with an anhydride. These functional groups can be used to attach polymers, such as proteins or polynucleotides, by methods well known in the art. Additionally, they can be used to provide a substrate for oligonucleotide synthesis, again using well established methodologies. Accordingly, the AS/ES coating provides a useful, stable, high surface area support for various immunoassays and hybridization assays.

Fluorescence Enhancement on Beads

An advantage of the MTPs discussed above is that they can be used in assays reactions where MTPs with different attached probes are incubated in the same contacting fluids, and then the different results on the MTPs can be correlated to the specific probes by querying the MTP for its unique code. To a lesser extent, other beads can be similarly multiplexed using other technologies. For example, Luminex has fluorescence-coded microbeads.

In examining the surface structure that is believed to contribute to the results obtained with AS/ES coated substrate, it was concluded that the porous structure of the coating can provide a part of the explanation. Analogous surfaces are found on many of the beads (e.g., surface porous beads) used in assay formats. Accordingly, the invention further relates to beads with deposited metal particles. The particles can be deposited by, for example, any of the methods described above.

The beads utilized in assay formats are typically engineered to have carboxylic acid or amine functionality. In the manner described above, this functionality can be used to anchor the AS/ES polymer, such that the metal particles are stabilized and/or protected.

Metal Particles on Metal Layers

In certain embodiments, metal particles are applied directly to thin metal layers, and the combination can be stabilized with silane-based polymer. Thin metal layers can be formed for example by, for example, electroplating.

Assays

The fluorescence-enhanced surfaces described herein can be used in various assays, such as multiplex assays in which multiple assay probes are jointly processed, and thereafter distinguished by location, marking or transponder signal. Or, they can be used in more traditional assays such as in microtiter plates. Generally, with microtiter plates, a surface (e.g., the top of the bottom surface) will be made into a fluorescence-enhanced surface. The AS/ES polymer provides a stable support for spatially resolved synthesis of polynucleotides, or spatially resolved deposition of polynucleotides or proteins. As such, a fluorescence-enhanced multiplex assay can be conducted on Nucleic acid/protein arrays. For the purpose of describing such arrays, the different areas with distinct probes can be designated "substrates." Thus, the substrates of the wells or different regions of the array can comprise "substrates," wherein a plurality of the substrates have unique probes affixed thereto.

When an assay is conducted with microchips or microtabs, the microchips or microtabs will generally be subjected to highly abrasive conditions, such as when a microcentrifuge tube is vortexed or centrifuged. Such entities, when treated with a polymer top coating have been found to be sufficiently stable to such abuse to allow for such assaying. Methods can identify the probe on a microtransponder by querying with light or radio waves, as appropriate.

Misc.

In certain embodiments, the fluorescence enhancement achieved (comparing metal particle coated substrates with their reasonably nearest analogs without particles) is 10-fold or more, or 20-fold or more, or 30-fold or more, or 40-fold or more. Or, in certain embodiments, the fluorophore lifetime is decreased, such as 5-fold or more, or 10-fold or more, or 15-fold or more, or 20-fold or more.

The fluorescence enhancement is typically in reference to a surface-mediated fluorescence assay. This terminology refers to assays where the color/fluorescence-generating chemistry occurs predominately on the surface of a substrate. The substrate may be coated with polymer, in which case the "surface" is interpreted as the polymer surface. Where the polymer coating is porous, the surface includes pores (though obviously if they are so deep as to obscure the fluorescence then that portion may be functionally insignificant).

EXAMPLE 1

Coating MTPs with AS/ES

MTPs were pretreated with 99.5% methyl alcohol at room temperature (RT) for 10 min, and repeated three times. The MTPs were then rinsed with 0.01% distilled water and 0.9% aminopropyltriethoxysilane (APTS) in dry toluene/dimethylformamide (DMF) mixture at RT, and the rinse repeated four times. After rinsing, MTPs were immediately treated with a coating solution (mixture of 0.01% distilled water, 0.9% APTS, and 0.3% 3-glycidoxypropyltrimethoxysilane (GPTS) in dry toluene and DMF at 80° C. for 45 min, then repeated once. After the coating reaction, MTPs were washed once with toluene, three times with DMF, and three times with acetonitrile at RT, followed by air drying. The procedure placed both amino and hydroxy groups on the surface of MTPs.

EXAMPLE 2

Amino to Carboxylic Acid Conversion

Amino-derivatized MTPs were treated with 10% succinic anhydride in dry pyridine:DMF (1:9) on a tissue culture rotator at RT for 30 min. This step was repeated once using fresh reagents. After the reaction, the carboxylated MTPs were washed with DMF four times and acetonitrile twice, followed by air drying.

EXAMPLE 3

Silver Island Film on MTPs

Silver island film (SIF) was deposited on the surface of carboxylated MTPs as reported in Matveeva et al., with several modifications. Two drops of 5% NaOH was progressively added to 6 ml of 0.83% $AgNO_3$ solution with intensive stirring at RT in a 15 ml reaction tube. 0.2 ml of 30% $NH_4OH$ was subsequently added with intensive stirring at RT. The clear solution was incubated in an ice bath for 10 min, followed by the addition of 1.5 ml of a 4.8% fresh glucose solution with intensive stirring. Carboxylated MTPs were incubated in this solution in an ice bath for 2 min, and then on a tissue culture rotator at RT for 20 min. After the silver deposition, MTPs were immediately washed with distilled water three times followed by air drying.

EXAMPLE 4

Measuring Fluorescence Decay

Fluorescence decay of Alexa Fluor 555 (AF555) deposited on MTPs was measured on a FluoTime 200 fluorometer (PicoQuant) using excitation from a pulsed picosecond 475 nm solid state laser. The instrument was equipped with a microchannel plate photomultiplier (MCP) ultrafast detector, a monochromator and a polarizer in the detection path. Two 550 nm long wave pass filters were used on the emission optics for observation at 600 nm to eliminate scattered excitation light. For measurements, MTP were placed between two cover slips and mounted in a front face attachment. Fluorescent lifetime data were analyzed with a FluoFit version 4 software (Picoquant) and fitted to a multi-exponential model.

EXAMPLE 5

Antibody Conjugation

To protect SIF from scratches, a thin layer of polymer (20 min polymer coating, see above) was deposited onto SIF-MTP and carboxylated prior to performing the immunoassays. To conjugate the antibody to MTPs, ethyl-3-(3-dimethylaminopropyl)-carbodiimide (EDC) was allowed to react with carboxyl groups on the surface of the polymer-coated MTPs to form an O-acylisourea intermediate. The intermediate was stabilized in aqueous solution by reacting with N-hydroxysuccinamide (NHS), resulting in an NHS-activated site. The intermediate was then reacted with primary amines on protein to form amide bonds, as outlined below.

The carboxylated SIF or non-SIF-MTPs were incubated with 50 mg/ml 1-EDC and 50 mg/ml NHS in 0.1M HEPES buffer (pH 7.5) on a rotator for 30 min at RT. The MTPs were then washed with 60 µl PBS three times and incubated with 200 µg/ml monoclonal anti-human IL-6 antibody (R&D Systems) for 30 min at RT on a tissue culture rotator. The MTPs were washed with PBS three times and blocked with SuperBlock solution (Thermo Scientific) for 5 min at RT on a rotator. This blocking step was repeated twice. The MTPs were then washed with PBS three times (2 min each) and stored in PBS with 1% BSA at 4° C.

EXAMPLE 6

Immunoassay

Anti-IL-6-conjugated MTPs were incubated with 50 µl recombinant human IL-6 standard (R&D Systems) in PBS with 1% BSA for 1.5 hour at RT on a rotator. After incubation, the MTPs were washed with Tris-buffered saline Tween-20 (TBST) three times.

The detection antibody solution was prepared by diluting biotinylated anti-human IL-6 antibody (R&D System) to 5.0 µg/ml with 1% BSA in PBS. The MTPs were then incubated with 50 µl of detection antibody for 1 hour, followed by washing with TBST three times. The MTPs were pooled and incubated with 50 µl of 8 µg/ml SA-PE in PBS for 15 min at RT in the dark. After incubation, the MTPs were washed with TBST three times and distilled water twice, and air dried. PE fluorescence was confirmed using a fluorescent microscope (Nikon Eclipse E600 with Y-FL EPI fluorescence attachment) and quantified with Image J software (NIH).

The assay sensitivity is defined as the minimum IL-6 concentration producing a signal equal to three deviations (SD) from the standard zero. This represents the lowest value read from the standard curve that can be statistically distinguished from zero. To determine the assay sensitivity, a standard curve was generated using Prism 5.0 software: three standard SDs for the standard zero were added to the mean fluorescence for the standard zero replicates (six replicates for non-SIF and nine replicates for SIF) and the corresponding concentration was determined from the standard curve.

A 25-fold increase in sensitivity over the method not involving a SIF was obtained.

EXAMPLE 7

DNA Assay

Carboxylated SIF or non-SIF-MTPs were conjugated with 50 g/ml avidin (see Immunoassay section above) and incubated with 10 M 5'-biotinylated probe oligonucleotides on a tissue culture rotator at RT for 1 hour. The MTPs were then washed with TE buffer three times at RT, and stored in Tris/EDTA (TE) buffer at 4° C. The sequence of the oligonucleotide probe was: 5'-biotin-TTTTTTTTTGCTTTCCT-TCACTG-3' (SEQ ID NO:1). As a negative control, another probe with a point T/C mutation (underlined) was used: 5'-biotin-TTTTTTTTTCTTTCCTCCACTGT-3' (SEQ ID NO:2).

In preparation for hybridization, oligonucleotide-linked MTPs were incubated in 1× pre-hybridization buffer at 45° C. for 10 min. After removing the pre-hybridization buffer, the MTPs were incubated in 1× hybridization solution that contained 5'-Cy3-labeled target oligonucleotides for 2 hours at 45° C. in a hybridization oven (Bambino, Boekel Scientific), in the dark. The sequence of the target oligonucleotide was: 5'-Cy3-AATAACTTTGCAACAGTGAAGGAAAGC-CTTTGG A-3' (SEQ ID NO:3). The target and probe oligonucleotides contained a perfectly matched sequence of 14 nt (underlined). After hybridization, MTPs were rinsed twice with a pre-warmed (45° C.) 1× washing buffer and incubated in a fresh 1× washing buffer at 45° C. for 30 min. Then the MTPs were washed with distilled water three times at RT and air dried. Images of fluorescent MTPs were taken with a digital camera attached to the fluorescent microscope and the intensity quantified.

The pre-hybridization buffer contained 50 mM Tris-HCl (pH 8.0), 150 mM NaCl, 0.1% SDS, 0.5% Ficoll (type 400), 5 mM EDTA, 200 µg/ml sheared, denatured salmon sperm DNA and 1 µg/µl BSA. The 1× hybridization solution contained 50 mM Tris-HCl (pH 8.0), 150 mM NaCl, 0.1% SDS, 5 mM EDTA(pH 8.0) and 50 µg/ml sheared, denatured salmon sperm DNA. Washing buffer was 50 mM Tris-HCl (pH 8.0) containing 150 mM NaCl and 0.1% SDS.

A 38-fold increase in sensitivity over the method not involving a SIF was obtained.

EXAMPLE 8

Effects of BSA-Biotin-Avidin Layers

It is well known that the distance between silver nanoparticles and the fluorophore is important for enhancement. To investigate the role of metal-to-fluorophore distance in fluorescence enhancement on polymer-coated MTPs, alternating layers of BSA-biotin and avidin were used. BSA has previously been shown to absorb as a monolayer onto silver surfaces. The MTPs did not have a polymer top coating. The first BSA-biotin layer on SIF-MTPs was formed by incubating SIF-MTPs with 1 mg/ml BSA-biotin for 1 hr and then washed with PBS three times. The MTPs were then incubated with 1 mg/ml avidin for 40 min to allow the binding between avidin and biotin, and washed with PBS three times. High concentrations (1 mg/ml) of BSA-biotin and avidin were used to ensure that the MTP surface was saturated. The procedure was repeated to build multiple BSA-biotin-avidin layers. Biotinylated and AF555-labeled BSA were added as the final protein layer. The thickness of one biotin-BSA-avidin layer can be estimated as approximately 10 nm (diameters of both avidin and BSA approximated by a sphere are 5.5 nm, a diameter of a sphere corresponding to the molecular weight ($M_r$) of the BSA-avidin conjugate, i.e., 135 kDa, is 7 nm). Ten biotin-BSA-avidin layers were prepared to simulate the distance ranges from 10 to approximately 100 nm. As the data in FIGS. 1A and 1B indicate, no significant changes in fluorescence enhancement as a function of the metal-to-fluorophore distance was observed. The enhancement varied 5 to 10-fold over the entire range investigated, though a spike was observed at the lowest distance tested, which corresponded to the direct deposition of the fluorescent molecule on the SIF-MTPs. This is in contrast to the results reported by Malicka et al., *Anal. Biochem.* 315 (2003) 57-66 and Fu et al. *J. Phys. Chem. B* 110 (2006) 22557-22562, where the highest fluorescence enhancement was observed when the proximity of fluorophore molecules to SIF on a glass or quartz surface was approximately 5 nm to 10 nm (one BSA-avidin layer) and the enhancement ratio dropped from 11- to 4-fold (Malicka et al.) or from 110- to 2-fold (Fu et al.) as the number of BSA-avidin layers increased from 1 to 3.

Numbered Embodiments

The invention includes without limitation the following numbered embodiments:

1. A fluorescence enhancing substrate comprising:
   a substrate;
   a first coating of AS/ES on the substrate, wherein the coating is thicker than monolayer; and
   metal particles deposited or formed on the AS/ES coating, said particles effective to enhance a surface-mediated fluorescence assay by 5-fold or more,
   optionally wherein the metal particles stabilized or protected with a coating or further coating of polymer, and
   optionally wherein the substrate is a microtab.

2. A fluorescence enhancing substrate comprising:
   a polymeric assay bead having surface pores; and
   metal particles deposited or formed on the surface of the bead, said particles effective to enhance a surface-mediated fluorescence assay by 5-fold or more.

3. The fluorescence enhancing substrate of one of embodiments 1-2, wherein AS is according to formula I:

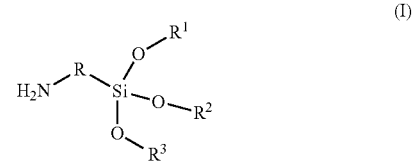

wherein R is a moiety of carbon, hydrogen and oxygen such that the linkage to the nitrogen is C—N, and the linkage to the silicon is C—Si; and
   wherein $R^1$, $R^2$ and $R^3$ are independently moieties of carbon, hydrogen and oxygen such that the linkage to the illustrated oxygen is C—O and the so-defined silicon ethers are reactive with silicate glass; and
   ES is according to formula II:

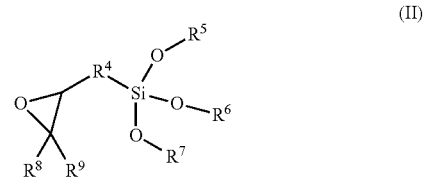

wherein $R^4$ is a moiety of carbon, hydrogen and oxygen such that the linkage to the silicon is C—Si;
   wherein $R^5$, $R^6$ and $R^7$ are independently moieties of carbon, hydrogen and oxygen such that the linkage to the illustrated oxygen is C—O and the so-defined silicon ethers are reactive with silicate glass; and
   wherein $R^8$ and $R^9$ are independently H or C1 to C4 alkyl.

4. An assay comprising:
   conducting a fluorescence-developing assay in a plurality of wells of a microtiter plate or with a nucleic acid/protein array, the microtiter wells or different regions of the array comprising substrates according to one of embodiments 1 or 3, wherein a plurality of the substrates have unique probes affixed thereto; and
   measuring the fluorescence associated with the substrates and identifying the correlated probe by location.

5. A multiplex assay comprising:
   conducting a fluorescence-developing assay on microtabs having substrates according to one of embodiments 1 or 3-4, wherein a plurality of the microtabs have unique probes affixed to their substrates; and
   measuring the fluorescence associated with the substrates and identifying the correlated probe,
   optionally wherein the microtabs are MTPs that send a unique identifier, and the correlated probe is identified by querying the MTPs for their identifiers.

6. A polymer coating on a substrate comprising:
the substrate; and
the polymer coating formed from reacting AS and AE with the substrate, wherein AS is according to formula I:

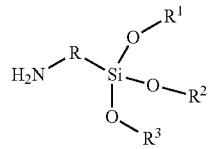

(I)

wherein R is a moiety of carbon, hydrogen and oxygen such that the linkage to the nitrogen is C—N, and the linkage to the silicon is C—Si; and
wherein $R^1$, $R^2$ and $R^3$ are independently moieties of carbon, hydrogen and oxygen such that the linkage to the illustrated oxygen is C—O and the so-defined silicon ethers are reactive with silicate glass; and
ES is according to formula II:

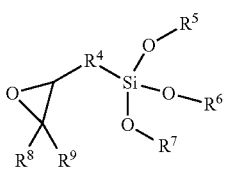

(II)

wherein $R^4$ is a moiety of carbon, hydrogen and oxygen such that the linkage to the silicon is C—Si;
wherein $R^5$, $R^6$ and $R^7$ are independently moieties of carbon, hydrogen and oxygen such that the linkage to the illustrated oxygen is C—O and the so-defined silicon ethers are reactive with silicate glass; and
wherein $R^8$ and $R^9$ are independently H or C1 to C4 alkyl, optionally wherein the coating is formed with AS and ES used in an AS:ES ratio of 2:1-5:1 (molar),
optionally wherein the coating layer is 0.5 micron or more thick.

7. The polymer coating of embodiment 6, formed with aminopropyltrimethoxysilane or aminopropyltriethoxysilane and 3-glycidoxypropyltrimethoxysilane.

8. A method of forming polymer coating on a substrate comprising:
reacting AS and AE with the substrate,
wherein AS is according to formula I:

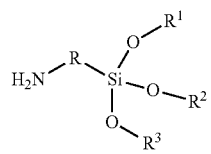

(I)

wherein R is a moiety of carbon, hydrogen and oxygen such that the linkage to the nitrogen is C—N, and the linkage to the silicon is C—Si; and
wherein $R^1$, $R^2$ and $R^3$ are independently moieties of carbon, hydrogen and oxygen such that the linkage to the illustrated oxygen is C—O and the so-defined silicon ethers are reactive with silicate glass; and ES is according to formula II:

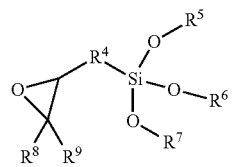

(II)

wherein $R^4$ is a moiety of carbon, hydrogen and oxygen such that the linkage to the silicon is C—Si;
wherein $R^5$, $R^6$ and $R^7$ are independently moieties of carbon, hydrogen and oxygen such that the linkage to the illustrated oxygen is C—O and the so-defined silicon ethers are reactive with silicate glass; and
wherein $R^8$ and $R^9$ are independently H or C1 to C4 alkyl.

9. The method of embodiment 8, wherein the reacting is maintained or repeated until a thickness of 0.5 micron or more is achieved.

10. A method of forming a fluorescence enhancing substrate comprising:
applying a first coating of AS/ES on the substrate, wherein the coating is thicker than monolayer; and
depositing metal particles on the AS/ES coating by reducing metal salts, wherein said reduction-formed particles are effective to enhance a surface-mediated fluorescence assay by 5-fold or more.

11. A multiplex assay comprising:
conducting a fluorescence-developing assay on microtabs having at least one surface that shows plasmonic enhancement, wherein a plurality of the microtabs have unique probes affixed to their plasmonically enhanced surfaces; and
measuring the fluorescence associated with the substrates and identifying the correlated probe by for the microtab.

12. The assay of embodiment 11, wherein metal particles providing the plasmonic enhancement are stabilized with a polymer.

13. The assay of one of embodiments 11-12, wherein the microtabs are MTPs that send a unique identifier, and the correlated probe is identified by querying the MTPs for their identifiers.

14. The assay of one of embodiments 11-13, wherein the microtab is plasmonically enhanced by having a surface coated with a metal layer, on which are metal particles.

15. The assay of one of embodiments 11-14, wherein the microtab is plasmonically enhanced by having a surface on which are metal particles.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While the foregoing is directed to embodiments of the present invention, other and further embodiments of the invention may be devised without departing from the basic scope thereof, and the scope thereof is determined by the claims that follow. Any claim below that is written as dependent on an independent claim can also be written as dependent on any of the claims under such independent claim, except where logic forecloses such a dependency.

What is claimed is:

1. A fluorescence enhancing substrate configured to covalently attach assay reagent comprising:
 a substrate;
 a first coating comprising AS and ES (AS/ES) on the substrate, wherein the coating is thicker than monolayer; and
 metal particles deposited or formed on the AS/ES coating, said particles effective to enhance a surface-mediated fluorescence assay by 5-fold or more, wherein AS is a reactive amine that is not a tertiary amine, and wherein the substrate with its first coating and any additional AS/ES coating(s) has amine and hydroxy functionality from AS and ES available for attaching an assay useful amount of the assay reagent.

2. The fluorescence enhancing substrate of claim 1, wherein the metal particles are stabilized or protected with a coating or further coating of polymer.

3. The fluorescence enhancing substrate of claim 1, wherein the substrate is a microtab that is a light-triggered transponder.

4. An assay comprising:
 conducting a fluorescence-developing assay in a plurality of wells of a microtiter plate or with a nucleic acid or protein array, the microtiter wells or different regions of the array comprising substrates according to claim 1, wherein a plurality of the substrates have unique probes affixed thereto; and
 measuring the fluorescence associated with the substrates and identifying the correlated probe by location.

5. A multiplex assay comprising:
 conducting a fluorescence-developing assay on microtabs having substrates according to claim 1, wherein a plurality of the microtabs have unique probes affixed to their substrates; and
 measuring the fluorescence associated with the substrates and identifying the correlated probe.

6. The fluorescence enhancing substrate of claim 1, wherein AS is according to formula I:

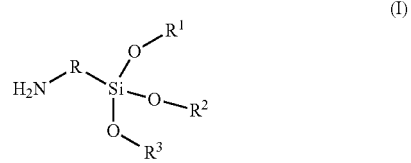

(I)

wherein R is a moiety of carbon, hydrogen and optionally oxygen such that the linkage to the nitrogen is C—N, and the linkage to the silicon is C—Si; and wherein $R^1$, $R^2$ and $R^3$ are independently moieties of carbon, hydrogen and optionally oxygen such that the linkage to the illustrated oxygen is C—O and the so-defined silicon ethers are reactive with silicate glass; and ES is according to formula II:

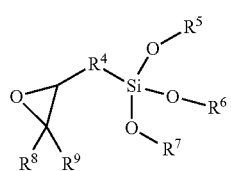

(II)

wherein R⁴ is a moiety of carbon, hydrogen and optionally oxygen such that the linkage to the silicon is C—Si;

wherein $R^5$, $R^6$ and $R^7$ are independently moieties of carbon, hydrogen and optionally oxygen such that the linkage to the illustrated oxygen is C—O and the so-defined silicon ethers are reactive with silicate glass; and wherein $R^8$ and $R^9$ are independently H or C1 to C4 alkyl.

7. An assay comprising:
conducting a fluorescence-developing assay in a plurality of wells of a microtiter plate or with a nucleic acid or protein array, the microtiter wells or different regions of the array comprising substrates according to claim 6, wherein a plurality of the substrates have unique probes affixed thereto; and
measuring the fluorescence associated with the substrates and identifying the correlated probe by location.

8. A multiplex assay comprising:
conducting a fluorescence-developing assay on microtabs having substrates according to claim 6, wherein a plurality of the microtabs have unique probes affixed to their substrates; and
measuring the fluorescence associated with the substrates and identifying the correlated probe.

9. The multiplex assay of claim 8, wherein the microtabs are MTPs that send a unique identifier, and the correlated probe is identified by querying the MTPs for their identifiers.

10. A method of forming a fluorescence enhancing substrate of claim 1, comprising:
applying a first coating of AS/ES on the substrate, wherein the coating is thicker than monolayer; and
depositing metal particles on the AS/ES coating by reducing metal salts, wherein said reduction-formed particles are effective to enhance a surface-mediated fluorescence assay by 5-fold or more.

11. A method of forming a fluorescence enhancing substrate of claim 10, wherein applying a first coating of AS/ES on the substrate comprises:
reacting AS and ES with the substrate, wherein AS is according to formula I:

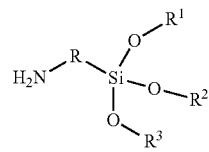

(I)

wherein R is a moiety of carbon, hydrogen and optionally oxygen such that the linkage to the nitrogen is C—N, and the linkage to the silicon is C—Si; and wherein $R^1$, $R^2$ and $R^3$ are independently moieties of carbon, hydrogen and optionally oxygen such that the linkage to the illustrated oxygen is C—O and the so-defined silicon ethers are reactive with silicate glass; and ES is according to formula II:

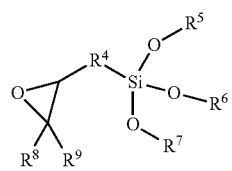

(II)

wherein R⁴ is a moiety of carbon, hydrogen and optionally oxygen such that the linkage to the silicon is C—Si;

wherein $R^5$, $R^6$ and $R^7$ are independently moieties of carbon, hydrogen and optionally oxygen such that the linkage to the illustrated oxygen is C—O and the so-defined silicon ethers are reactive with silicate glass; and wherein $R^8$ and $R^9$ are independently H or C1 to C4 alkyl.

12. The method of claim 11, wherein the reacting is maintained or repeated until a thickness of 0.5 micron or more is achieved.

13. The fluorescence enhancing substrate of claim 1, wherein the first coating is formed with AS and ES used in an AS:ES ratio of 2:1 molar or higher.

14. The fluorescence enhancing substrate of claim 1, wherein the first coating has a thickness of 0.1 micron or more.

15. The fluorescence enhancing substrate of claim 1, wherein the first coating has a thickness of 0.1 micron or more, and wherein the first coating has a porous structure.

16. The fluorescence enhancing substrate of claim 1, wherein the first coating has a thickness of 0.2 micron or more.

17. The fluorescence enhancing substrate of claim 1, wherein said particles are effective effective to enhance a surface-mediated fluorescence assay by 10-fold or more.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Synthetic oligomer

<400> SEQUENCE: 1
tttttttttg ctttccttca ctg                                              23

<210> SEQ ID NO 2
<211> LENGTH: 23
<212> TYPE: DNA
<213> ORGANISM: Artificial Sequence
<220> FEATURE:
<223> OTHER INFORMATION: Synthetic oligomer

<400> SEQUENCE: 2
tttttttttc tttcctccac tgt                                              23

<210> SEQ ID NO 3
<211> LENGTH: 33
<212> TYPE: DNA
<213> ORGANISM: Artificial Sequence
<220> FEATURE:
<223> OTHER INFORMATION: Synthetic oligomer

<400> SEQUENCE: 3
aataactttg caacagtgaa ggaaagcctt tgg                                   33